United States Patent
Blum

(10) Patent No.: US 9,102,605 B2
(45) Date of Patent: Aug. 11, 2015

(54) STABILIZED 3,3 DIALKOXY-1-PROPENE-PREPARATION

(76) Inventor: Holger Blum, Teufen (CH)

(*) Notice: Subject to any disclaimer, the term of this patent is extended or adjusted under 35 U.S.C. 154(b) by 314 days.

(21) Appl. No.: 13/824,209

(22) PCT Filed: Sep. 20, 2011

(86) PCT No.: PCT/EP2011/066335
§ 371 (c)(1),
(2), (4) Date: May 15, 2013

(87) PCT Pub. No.: WO2012/038433
PCT Pub. Date: Mar. 29, 2012

(65) Prior Publication Data
US 2013/0225869 A1    Aug. 29, 2013

(30) Foreign Application Priority Data
Sep. 21, 2010  (DE) .......................... 10 2010 037 691

(51) Int. Cl.
C07C 41/46   (2006.01)
A01N 35/02   (2006.01)
C02F 1/50    (2006.01)
C07C 41/58   (2006.01)

(52) U.S. Cl.
CPC ................ *C07C 41/46* (2013.01); *A01N 35/02* (2013.01); *C02F 1/50* (2013.01); *C07C 41/58* (2013.01); *C02F 2305/14* (2013.01)

(58) Field of Classification Search
USPC ...................................................... 568/581
See application file for complete search history.

(56) References Cited

U.S. PATENT DOCUMENTS

| 3,690,857 A | 9/1972 | Blair, Jr. |
| 5,183,944 A | 2/1993 | Werle et al. |
| 2008/0254082 A1* | 10/2008 | Toledano et al. ............. 424/408 |

FOREIGN PATENT DOCUMENTS

| DE | 102010037691 A1 | 3/2012 |
| WO | 96/15668 A1 | 5/1996 |
| WO | 96/25040 A1 | 8/1996 |

OTHER PUBLICATIONS

International Search Report for PCT Application No. PCT/EP2011/066335 dated Apr. 24, 2012.
International Preliminary Report on Patentability for PCT Application No. PCT/EP2011/066335 dated Apr. 4, 2013.

* cited by examiner

*Primary Examiner* — Rosalynd Keys
(74) *Attorney, Agent, or Firm* — Nixon Peabody LLP; Joseph Bach, Esq.

(57) ABSTRACT

Stabilized 3,3 dialkoxy-1-propene-preparation containing a compound of the formula I

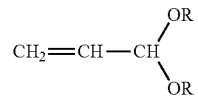

wherein R=C1-C6 hydrocarbon group
and a compound of the formula II $$Z \equiv (-R_1)_x (-OR_2)_y$$

where Z=C (carbon) or Si (silicon); R1=H or C1-C3 carbon group; R2=C1-C3 carbon group; x=0 or 1, x+y=4.

5 Claims, No Drawings

STABILIZED 3,3 DIALKOXY-1-PROPENE-PREPARATION

RELATED APPLICATIONS

This application is a National Phase of International Application No. PCT/EP2011/066335, entitled "STABILIZED 3,3 DIALKOXY-1-PROPENE-PREPARATION", which was filed on Sep. 20, 2011, and which claims priority of German Patent Application No. 10 2010 037 691.4, filed on Sep. 21, 2010 and the disclosures of which are hereby incorporated by reference herein in their entirety.

The invention relates to a stabilized 3,3 dialkoxy-1-propene preparation.

3,3 dialkoxy-1-propene is used in many different applications in order to free waters of any kind of unwanted organisms. For example, U.S. Pat. No. 3,690,857 teaches that the growth of aquatic plants in watery media and channels can be controverted without endangering the fish population thereby that 3,3 dialkoxy-1-propene is dosed into the water. This method serves to control a wide spectrum of organisms which are present in watery media and comprise aquatic plants, marine animals, algae, fungi, bacteria and the like. The watery media can cause problems in channels, ponds as well as in watering systems.

From U.S. Pat. No. 5,183,944 it is, furthermore, known that watery media, in particular in circulating systems, may be treated with acrolein, thereby that acrolein acetal is brought into contact with an acid, for example sulfuric acid, and that the gaseous acrolein generated thereby, is discharged by an inert gas from the deacetalation solution and is introduced into the watery medium to be treated as a gas in order to kill the organisms present in the medium.

In all these applications, it is a problem that the compound 3,3 dialkoxy-1-propene is to be stored as a starting material and is, therein, brought into contact with humidity.

Compounds of 3,3 dialkoxy-1-propene are non-poisonous, inflammable, clear liquids, having a characteristic, non-aggravating smell which compounds have gained importance in part also as food additives. In case 3,3 dialkoxy-1-propene is, however, brought into contact with humidity contaminated surfaces, it decomposes while forming the poisonous agent of acrolein which has the CAS 107-02-8. Furthermore, acrolein comprises characteristics of very much stimulating tears. Since, as it is well-known, all technical apparatuses in the vicinity of watery media which are used for delivering, storing and pre-dosing of liquids are in the wetted area more or less humidity contaminated after some period of operation, the practical application of compounds of the formula I is blocked by the simultaneous, excessively raised requirements for the labor protection of the operating personnel.

Occurrence of free acrolein is accompanied by a coloring reaction, accompanied by a diminishment of the active component. Experiments have shown that the speed with which the compounds of the formula I upon contact with humidity contaminated surfaces is splitting off acrolein, is increasing in the sequence from sweet water to brack water to see water.

It is an object of the invention, to provide the active substance 3,3 dialkoxy-1-propene in form of a preparation which withstands the splitting off of acrolein upon storage/delivery/conveyance in humidity contaminated apparatuses.

This object is achieved by the liquid, stabilized 3,3 dialkoxy-1-propene preparation containing a compound of the formula I

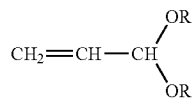

wherein R=C1-C6 hydrocarbon group, and wherein the preparation contains additionally a compound of the formula II

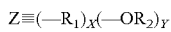

where Z=C (carbon) or Si (silicon); R1=H or C1-C3 carbon group: R2=C1-C3 carbon group; x=0 or 1, x+y=4.

The liquid stabilized dialkoxy-1-propene preparation is stabilized to such an extent that it may be applied by means of a humidity contaminated apparatus consisting of storage tanks, tube conduits, armatures and dosing pumps without acrolein being freed to a noticeable extend. Since the preparation withstands the splitting off of acrolein in humidity contaminated apparatuses, the coloring reaction in conjunction with a diminishing of the active substance is counteracted.

Compounds of the formula II are non-poisonous liquids having a weak partly pleasant smell, which compounds may be mixed in any percentage with compounds of the formula I.

It is an advantage that the application of compounds of the formula II as components of a preparation does not endanger the fish population in watery media or in channels.

According to an advantageous embodiment of the invention, the stabilized dialkoxy-1-propene preparation is characterized in that R1 equals H and/or that R2 equals C1 or C2. Because of the low molecular weight of these preparations, a reduction of the required amount of the compound of the formula II for stabilization is resulting.

According to an advantageous embodiment of the invention, the stabilized 3,3 dialkoxy-1-propene preparation is characterized in that the molar portion of the compound of the formula II in the preparation amounts to about 0.5 to 5 mol %.

The invention is now explained with reference to the following examples:

EXAMPLE 1 a) For producing a liquid PREPARATION A, as an active medium, the compound 3,3 dimethoxy-1-propene, having the CAS number 6044-68-4 was mixed with the inventive stabilizer, the compound 1,1,1 trimethoxy-methane with the CAS number 149-73-5, so that the ready-made mixture contained 98 mol % active substance and 2 mol % stabilizer. Accordingly, 100 gram of the PREPARATION A contain 2.1 gram stabilizer.

b) The PREPARATION made in this way, was subsequently tested in order to find out whether free acrolein is generated on storage in an humidity contaminated apparatus.

The testing apparatus consists of a 1-inch tube double fitting DIN 2982, material stainless steel AISI 316, having an interior diameter of 25.7 mm and a tube length of 220 mm. The tube is closed on both sides by a i-inch-hexagon cap, similar to DIN 2921, while using a Teflon sealing band, after it had been filled with 0.15 ml filtered sea water from the south port of the German Northern sea island of Helgoland. The testing apparatus prepared in this way, was stored in an horizontal position for three weeks at 18 degree Celsius so that the humidity could distribute completely on the inner stainless steel surface of the testing tube.

Subsequently to this preparation phase, one of the two hexagonal caps was opened and 100 ml of the PREPARA- TION described under a) was filled into the tube, and then, the hexagonal tube cap was again applied using a Teflon sealing band. The humid testing apparatus as closed in this way and filled with the PREPARATION was stored for further three weeks at 18 degree temperature.

Subsequently to this reaction phase, the testing apparatus was opened and about 1 ml portion of the liquid content of the tube was put into a petri dish for analyzing purposes.

The evaluation of the sample was made by means of olfactometry by means of the following justification scale:
Rating degree 0 (no noticeable agrolein smell, smell of the sample like the one of the original preparation)
Rating degree 1 (noticeable agrolein smell, moderate stimulation of tears)
Rating degree 2 (strong agrolein smell, very heavy stimulation of tears)

EXAMPLE 2

For producing a liquid PREPARATION B, as an active medium, the compound 3,3 dimethoxy-1-propene, having the CAS number 6044-68-4 was mixed with the inventive stabilizer, the compound 1,1,1 trimethoxy-methane with the CAS number 149-73-5, so that the ready-made mixture contained 95 mol % active substance and 5 mol % stabilizer. Accordingly, 100 gram of the PREPARATION B contain 5.2 gram stabilizer.

The PREPARATION was subjected to the same testing procedure as described in example 1, part b).

EXAMPLE 3

For producing a liquid PREPARATION C, as an active medium, the compound 3,3 dimethoxy-1-propene, having the CAS number 3054-95-3 was mixed with the inventive stabilizer, the compound 1,1,1 triethoxy-methane with the CAS number 122-51-0, so that the ready-made mixture contained 98 mol % active substance and 2 mol % stabilizer. Accordingly, 100 gram of the PREPARATION C contain 2.3 gram stabilizer.

The PREPARATION was subjected to the same testing procedure as described in example 1, part b).

EXAMPLE 4

For producing a liquid PREPARATION D, as an active medium, the compound 3,3 dimethoxy-1-propene, having the CAS number 3054-95-3 was mixed with the inventive stabilizer, the compound 1,1,1 triethoxy-methane with the CAS number 122-51-0, so that the ready-made mixture contained 95 mol % active substance and 5 mol % stabilizer. Accordingly, 100 gram of the PREPARATION D contain 5.7 gram stabilizer.

The PREPARATION was subjected to the same testing procedure as described in example 1, part b).

EXAMPLE 5

For producing a liquid PREPARATION E, as an active medium, the compound 3,3 dimethoxy-1-propene, having the CAS number 3054-95-3 was mixed with the inventive stabilizer, the compound 1,1,1 triethoxy-methane with the CAS number 78-39-7, so that the ready-made mixture contained 95 mol % active substance and 5 mol % stabilizer. Accordingly, 100 gram of the PREPARATION E contain 6.2 gram stabilizer.

The PREPARATION was subjected to the same testing procedure as described in example 1, part b).

EXAMPLE 6

For producing a liquid PREPARATION F, as an active medium, the compound 3,3 dimethoxy-1-propene, having the CAS number 3054-95-3 was mixed with the inventive stabilizer, the compound 1,1,1,1 tetraethoxy-methane with the CAS number 78-09-1, so that the ready-made mixture contained 98 mol % active substance and 2 mol % stabilizer. Accordingly, 100 gram of the PREPARATION F contain 2.9 gram stabilizer.

The PREPARATION was subjected to the same testing procedure as described in example 1, part b).

EXAMPLE 7

For producing a liquid PREPARATION G, as an active medium, the compound 3,3 dimethoxy-1-propene, having the CAS number 6044-68-4 was mixed with the inventive stabilizer, the compound 1,1,1,1 tetraethoxy-methane with the CAS number 1850-14-2, so that the ready-made mixture contained 98 mol % active substance and 2 mol % stabilizer. Accordingly, 100 gram of the PREPARATION G contain 2.1 gram stabilizer.

The PREPARATION was subjected to the same testing procedure as described in example 1, part b).

EXAMPLE 8

For producing a liquid PREPARATION H, as an active medium, the compound 3,3 dimethoxy-1-propene, having the CAS number 3054-95-3 was mixed with the inventive stabilizer, the compound 1,1,1,1 tetraethoxy-silane with the CAS number 78-10-4, so that the ready-made mixture contained 98 mol % active substance and 2 mol % stabilizer. Accordingly, 100 gram of the PREPARATION H contain 3.2 gram stabilizer.

The PREPARATION was subjected to the same testing procedure as described in example 1, part b).

COMPARATIVE EXAMPLE 1

For producing a liquid PREPARATION J, as an active medium, the compound 3,3 dimethoxy-1-propene, with CAS number 6044-68-4 as sole content agent was used.

The PREPARATION was subjected to the same testing procedure as described in example 1, part b).

COMPARATIVE EXAMPLE 2

For producing a liquid PREPARATION K, as an active medium, the compound 3,3 dimethoxy-1-propene, with CAS number 3054-95-3 as sole content agent was used.

The PREPARATION was subjected to the same testing procedure as described in example 1, part b).

COMPARATIVE EXAMPLE 3

For producing a liquid PREPARATION L as active agent, the compound 3,3 dimethoxy-1-propene, with CAS number 6044-68-4 was mixed with the compound 2,2 dimethoxy-propane with the CAS number 77-76-9, so that the ready-made mixture contained 95 mol % active substance and 5 mol % 2,2-dimethoxy-propane. Accordingly, 100 gram of the PREPARATION L contain 5.1 gram of 2,2-dimethoxy-propane.

The PREPARATION was subjected to the same testing procedure as described in example 1, part b).

COMPARATIVE EXAMPLE 4

For producing a liquid PREPARATION M as active agent, the compound 3,3 dimethoxy-1-propene, with CAS number 3054-95-3 was mixed with the compound 2,2 dimethoxy-propane with the CAS number 126-84-1, so that the ready-made mixture contained 95 mol % active substance and 5 mol % 2,2-dimethoxy-propane. Accordingly, 100 gram of the PREPARATION L contain 5.1 gram of 2,2-dimethoxy-propane.

The PREPARATION was subjected to the same testing procedure as described in example 1, part b).

The results are given in the following table 1:

TABLE 1

|  | Preparation | Rating degree | Color | Relative active agent content %* |
|---|---|---|---|---|
| Example |  |  |  |  |
| 1 | A | 0 | light | >99 |
| 2 | B | 0 | light | 98 |
| 3 | C | 0 | light | n.a. |
| 4 | D | 0 | light | >99 |
| 5 | E | 0 | light | n.a. |
| 6 | F | 0 | light | n.a. |
| 7 | G | 0 | light | >99 |
| 8 | H | 0 | light | >99 |
| Comparative example |  |  |  |  |
| 1 | J | 2 | colored | 78 |
| 2 | K | 2 | colored | 72 |
| 3 | L | 2 | colored | 68 |
| 4 | M | 1 | colored | 73 |

*Evaluation of contents by comparison with a freshly produced preparation.

As can be seen from Table 1, only the PREPARATIONS A to H which were produced according to the invention while using the compounds of formula II, were sufficiently protected against splitting off of acrolein upon storage/delivery/conveyance in moisture contaminated apparatuses.

Furthermore, the comparative samples J to K show, in addition to appearance of free acrolein, also a coloring reaction which is accompanied by a diminishing of the active agent content, as can be seen from the last column of Table 1.

The invention claimed is:

1. Stabilized 3,3 dialkoxy-1-propene-preparation containing a compound of the formula I

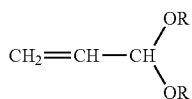

wherein R=C1-C6 hydrocarbon group, and wherein the preparation contains additionally a compound of the formula II

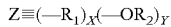

where Z=C (carbon) or Si (silicon); R1=H or C1-C3 carbon group; R2=C1-C3 carbon group; x=0 or 1, x+y=4.

2. Stabilized 3,3 dialkoxy-1-propene preparation according to claim 1, wherein R2 equals C1 or C2.

3. Stabilized 3,3 dialkoxy-1-propene preparation according to claim 1, wherein R1 equals H.

4. Preparation according to claim 1, wherein the molar portion of the compound of the formula II in the preparation amounts to about 0.5 to 5 mol %.

5. Stabilized 3,3 dialkoxy-1-propene preparation according to claim 3, wherein R2 equals C1 or C2.

* * * * *